(12) United States Patent
Grbic et al.

(10) Patent No.: US 11,244,453 B2
(45) Date of Patent: Feb. 8, 2022

(54) DETERMINING MALIGNANCY OF PULMONARY NODULES USING DEEP LEARNING

(71) Applicant: Siemens Healthcare GmbH, Erlangen (DE)

(72) Inventors: Sasa Grbic, Plainsboro, NJ (US); Dorin Comaniciu, Princeton Junction, NJ (US); Bogdan Georgescu, Plainsboro, NJ (US); Siqi Liu, Princeton, NJ (US); Razvan Ionasec, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 95 days.

(21) Appl. No.: 16/179,154

(22) Filed: Nov. 2, 2018

(65) Prior Publication Data
US 2020/0143540 A1    May 7, 2020

(51) Int. Cl.
| | | |
|---|---|---|
| G06T 7/00 | (2017.01) | |
| A61B 6/03 | (2006.01) | |
| A61B 6/00 | (2006.01) | |
| G06K 9/62 | (2006.01) | |

(52) U.S. Cl.
CPC ............ *G06T 7/0014* (2013.01); *A61B 6/032* (2013.01); *A61B 6/5217* (2013.01); *G06K 9/6228* (2013.01); *G06K 9/6256* (2013.01); *G06K 9/6267* (2013.01); *G06K 2209/053* (2013.01); *G06T 2207/10081* (2013.01); *G06T 2207/20081* (2013.01); *G06T 2207/20084* (2013.01); *G06T 2207/30064* (2013.01)

(58) Field of Classification Search
CPC ..... G06T 7/0014; A61B 6/032; A61B 6/5217; G06K 9/6228; G06K 9/6256
See application file for complete search history.

(56) References Cited

U.S. PATENT DOCUMENTS

| | | |
|---|---|---|
| 9,760,807 B2 | 9/2017 | Zhou et al. |
| 2016/0292855 A1* | 10/2016 | Metzger ................ G06T 7/0012 |
| 2017/0200067 A1* | 7/2017 | Zhou ...................... G06T 7/143 |
| 2018/0116620 A1 | 5/2018 | Chen et al. |
| 2018/0225823 A1 | 8/2018 | Zhou et al. |

OTHER PUBLICATIONS

Liao, Evaluate the Malignancy of Pulmonary Nodules Using the 3D Deep Leaky Noisy-or Network, arvix.org, https://arxiv.org/pdf/1711.08324.pdf, Nov. 22, 2017 (Year: 2017).*
Wu, Botong, et al. "Joint learning for pulmonary nodule segmentation, attributes and malignancy prediction." 2018 IEEE 15th International Symposium on Biomedical Imaging (ISBI 2018). IEEE, 2018. (Year: 2018).*

(Continued)

*Primary Examiner* — Vincent Rudolph
*Assistant Examiner* — Raphael Schwartz (57) ABSTRACT

Systems and method are described for determining a malignancy of a nodule. A medical image of a nodule of a patient is received. A patch surrounding the nodule is identified in the medical image. A malignancy of the nodule in the patch is predicted using a trained deep image-to-image network.

16 Claims, 9 Drawing Sheets

(56) References Cited

OTHER PUBLICATIONS

Mehta, Sachin, et al. "Y-Net: joint segmentation and classification for diagnosis of breast biopsy images." International Conference on Medical Image Computing and Computer-Assisted Intervention. Springer, Cham, Jun. 4, 2018. (Year: 2018).*

European Search Report dated Jan. 31, 2020 in corresponding European Patent Application No. 19206171.1.

Chen, et al.:"Lung Nodule Detection via 3D U-Net and Contextual Convolutional Neural Network", 2018 International Conference on Networking and Network Applications (NANA), IEEE, Oct. 12, 2018 (Oct, 12, 2018), pp. 356-361.

Zhang, et al: "A Pulmonary Nodule Detection Model Based on Progressive Resolution and Hierarchical Saliency", arxiv.org, Cornell University Library, 201 Olin Library Cornell University Ithaca, NY 14853, Jul. 2, 2018 (Jul. 2, 2018).

Nannan, et al: "Deep Convolutional Nets for Pulmonary Nodule Detection and Classification", Aug. 11, 2018 (Aug. 11, 2018), International Conference on Financial Cryptography and Data Security; [Lecture Notes in Computer Science; Lect.Notes Computer], Springer, Berlin, Heidelberg, pp. 197-208.

Lokhandwala et al., "Medicare costs analysis indicated need for decreasing use of biopsies as diagnosis tool for lung cancer", Chicago Multidisciplinary Symposium in Thoracic Oncology, Oct. 30, 2014; 5 pgs.

Zhou et al; "Cross-Domain Image Analysis and Cross-Domain Image Synthesis Using Deep Image-to-Image Networks and Adversarial Networks;" U.S. Appl. No. 15/872,408, filed Jan. 16, 2018.

Liu et al., "3D Anisotropic Hybrid Network: Transferring Convolutional Features from 2D Images to 3D Anisotropic Volumes", Dec. 4, 2017, University of Australia, 17 pgs.

Ghesu et al., "Multi-Scale Deep Reinforcement Learning for Real-Time 3D-Landmark Detection in CT Scans", IEEE Transactions on Pattern Analysis and Machine Intelligence, 14 pgs.

* cited by examiner

DETERMINING MALIGNANCY OF PULMONARY NODULES USING DEEP LEARNING

TECHNICAL FIELD

The present invention relates generally to determining malignancy of pulmonary nodules, and more particularly to determining malignancy of pulmonary nodules by analyzing medical images using machine learning models.

BACKGROUND

The current standard for screening a patient for lung cancer is computed tomography (CT) imaging. If pulmonary nodules are found in the CT imaging of the patient, a biopsy may be performed to retrieve portions of the nodules to determine their malignancy by histopathological examination. The decision to perform a biopsy is based on simple features of the CT imaging, such as the number of nodules, the size of the nodules, the shape of the nodules, and the growth of the nodules. However, such simple features of the CT imaging constitute a small amount of the total information available in the CT imaging. A significant amount of the information available in the CT imaging remains unused in determining whether to perform a biopsy.

Pulmonary biopsies are an expensive procedure to perform. For many patients who undergo biopsies, their nodules are found to be benign. Reducing the number of patients who undergo such unnecessary biopsies would result in significant medical cost savings, while also reducing patient exposure to unnecessary medical procedures.

BRIEF SUMMARY OF THE INVENTION

In accordance with one or more embodiments, systems and methods for determining a malignancy of a nodule are provided. A medical image of a nodule of a patient is received and a patch surrounding the nodule is defined in the medical image. A malignancy of the nodule in the patch is predicted using a trained deep image-to-image network. In one embodiment, the trained deep image-to-image network comprises a deep reasoner network.

In accordance with one embodiment, the deep image-to-image network is trained using training images depicting particular nodes and results of a histopathological examination of the particular nodules. The deep image-to-image network may additionally or alternatively be trained (e.g., where the results of the histopathological examination of the particular nodules are insufficient to train the deep image-to-image network) using additional training images depicting additional nodules and results of a radiologist examination of the additional nodules.

In accordance with one embodiment, the malignancy of the nodule is predicted by determining a score indicating the malignancy of the nodule or by classifying the nodule as malignant or not malignant. Based on the predicted malignancy of the nodule, another medical image of the nodule of the patient may be received. For example, the other medical image may be received in response to the predicted malignancy of the nodule (e.g., a score indicating a malignancy of the nodule) satisfying one or more thresholds. The other medical image may be a more detailed medical image of the nodule than the initial medical image. Another patch surrounding the nodule may be defined in the other medical image and the malignancy of the nodule in the other patch may be predicted using the trained deep image-to-image network.

In accordance with one or more embodiments, the trained deep image-to-image network may comprise an encoder and a decoder. The patch is input into the encoder and the encoder converts the patch to a low level representation. The decoder predicts the malignancy of the nodule in the patch from the low level representation.

These and other advantages of the invention will be apparent to those of ordinary skill in the art by reference to the following detailed description and the accompanying drawings.

DETAILED DESCRIPTION

The present invention generally relates to methods and systems for determining malignancy of pulmonary nodules using deep learning. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed by a computer system using data stored within the computer system.

Figure 1:
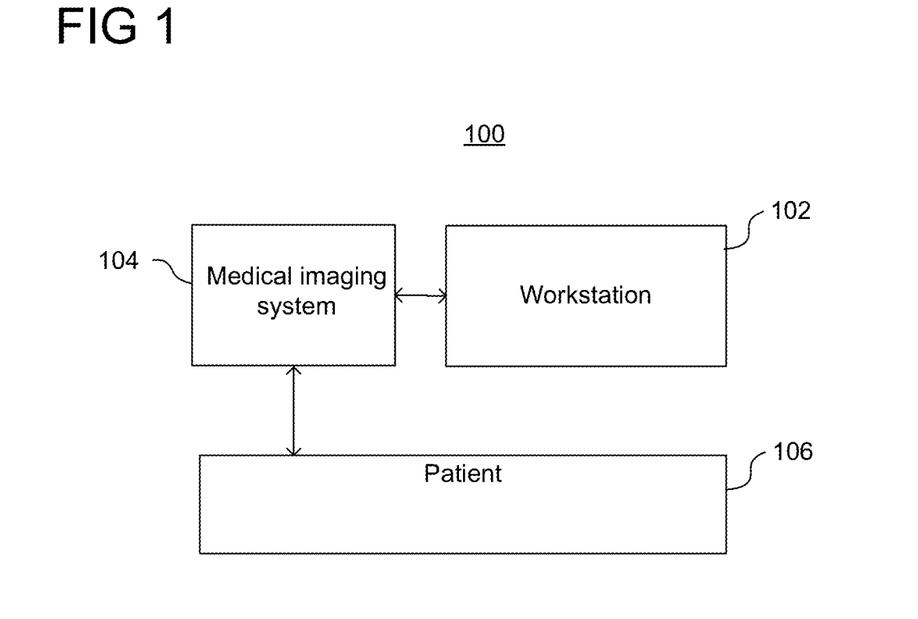
FIG. 1 shows an illustrative system for determining a malignancy of nodules, in accordance with one or more embodiments.

FIG. 1 shows a system 100 configured to determine or predict a malignancy of nodules, in accordance with one or more embodiments. System 100 includes workstation 102, which may be used for assisting a clinician (e.g., a doctor, a medical professional, or any other user) in performing a medical evaluation on a patient 106 (or any other subject). Workstation 102 may be implemented using any suitable computing device, such as, e.g., computer 902 of FIG. 9.

In one embodiment, workstation 102 may assist the clinician in screening patient 106 for lung cancer. Accordingly, workstation 102 may receive medical images of patient 106 from one or more medical imaging systems 104. Medical imaging system 104 may be of any modality, such as, e.g., a two-dimensional (2D) or three-dimensional (3D) computed tomography (CT), x-ray, magnetic resonance imaging (MRI), ultrasound (US), single-photon emission computed tomography (SPECT), positron emission tomography (PET), or any other suitable modality or combination of modalities. In another embodiment, workstation 102 may receive the images by loading previously stored images of the patient acquired using medical imaging system 104.

Embodiments of the present invention provide for the analysis of medical images using machine learning models to determine or predict a malignancy of pulmonary nodules. Advantageously, such machine learning models determine a malignancy of pulmonary nodules using features of the medical images that cannot be practically or possibly used in a human analysis under conventional clinical practice. Accordingly, embodiments of the present invention use additional information from the medical images to exclude a subset of patients who would have unnecessarily undergone biopsies under conventional clinical practices, thereby reducing medical costs and patient exposure to unnecessary medical procedures.

It should be understood that while the embodiments discussed herein may be discussed with respect to analyzing medical images to determine malignancy of pulmonary nodules of a patient, the present invention is not so limited. Embodiments of the present invention may be applied for analyzing any type of image for any measure of interest.

Figure 2:
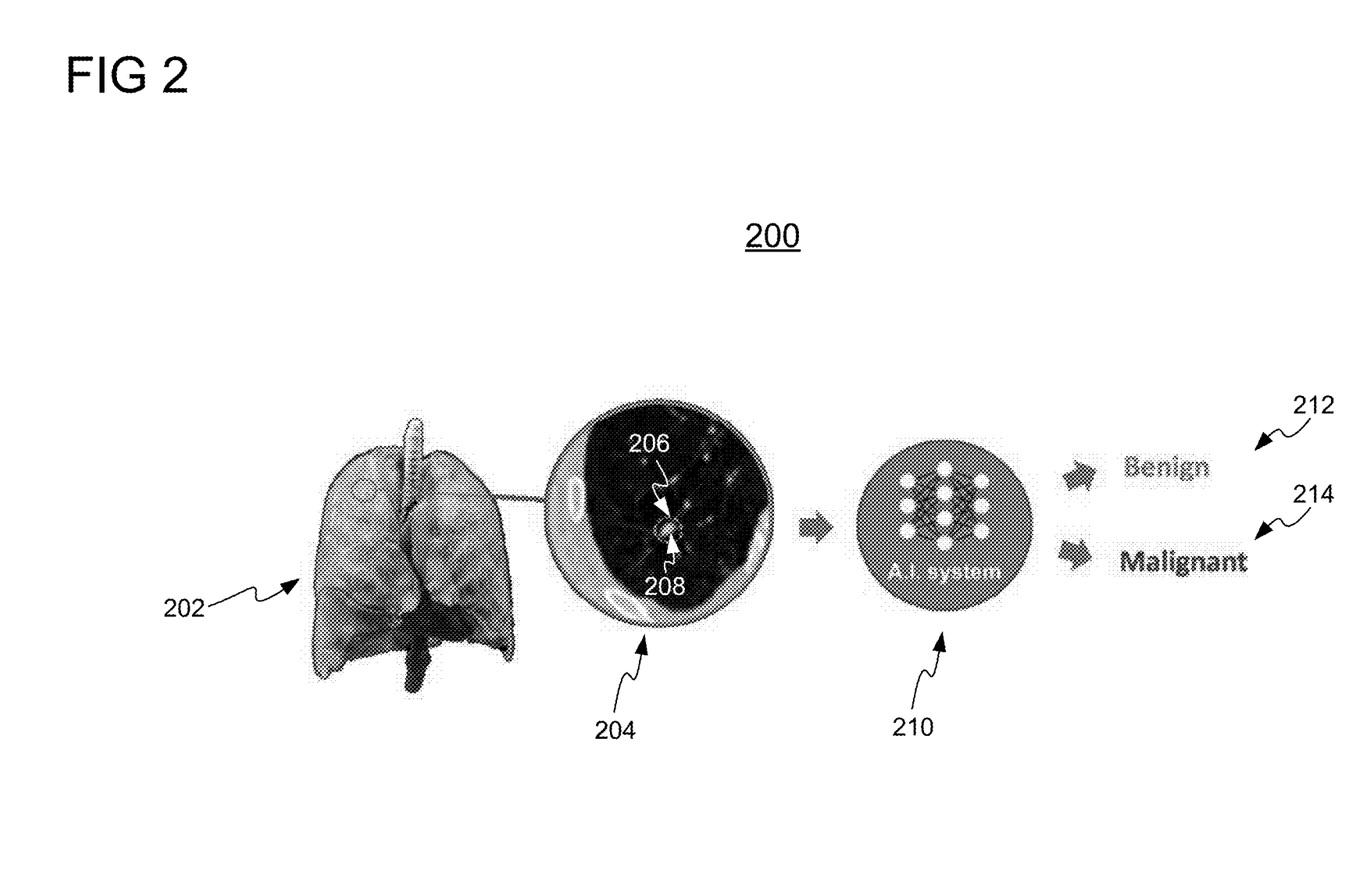
FIG. 2 shows a high-level workflow for predicting a malignancy of a pulmonary nodule, in accordance with one or more embodiments.

FIG. 2 shows a high-level workflow 200 for predicting a malignancy of a pulmonary nodule, in accordance with one or more embodiments. In workflow 200, a 3D CT medical image 202 of the lungs of a patient is analyzed to define a patch 206 encompassing a pulmonary nodule 208, as shown in exploded view 204 of medical image 204. Patch 206 encompassing pulmonary nodule 208 is input into artificial intelligence (A.I.) system 210, which outputs a prediction on the malignancy of pulmonary nodule 208. The prediction may be a classification of pulmonary nodule 208 as being malignant 214 or benign (i.e., not malignant) 212. A medical decision may be made based on the prediction. For example, if pulmonary nodule 208 is predicted to be malignant 214, the patient may undergo a biopsy of pulmonary nodule 208 for histopathological examination to confirm its malignancy.

Figure 3:
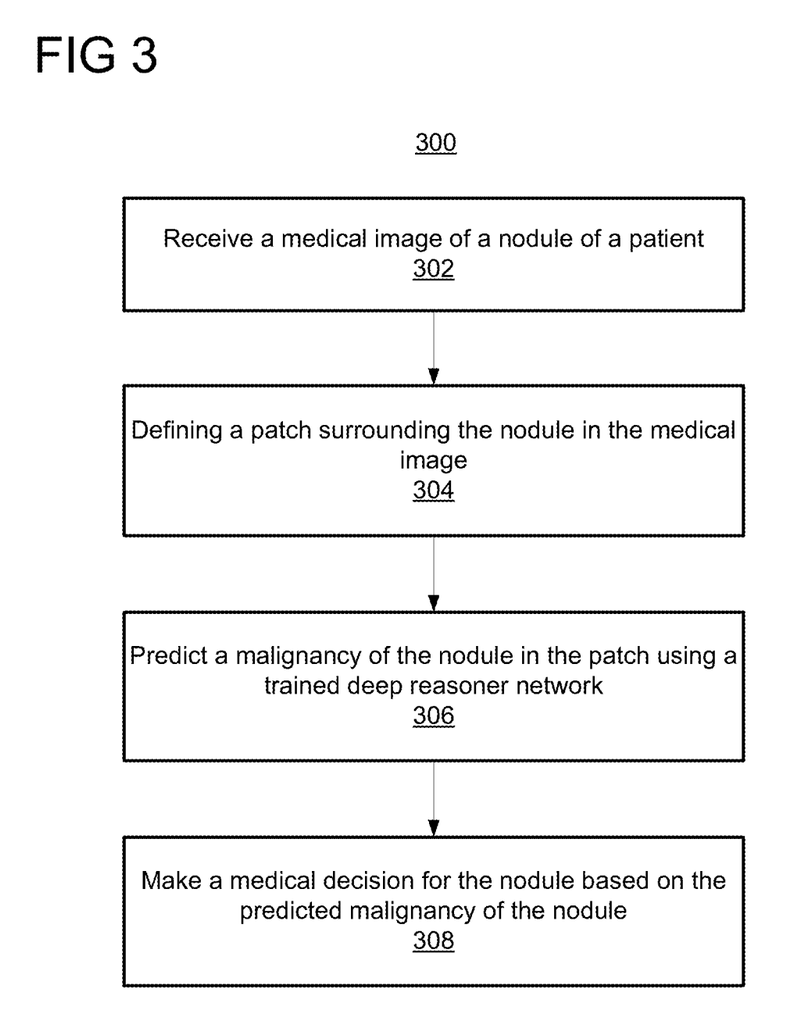
FIG. 3 shows a method for predicting a malignancy of a nodule of a patient, in accordance with one or more embodiments.

FIG. 3 shows a method 300 for predicting a malignancy of a nodule of a patient, in accordance with one or more embodiments. Method 300 will be discussed with respect to system 100 of FIG. 1. In one embodiment, the steps of method 300 are performed by workstation 102 of FIG. 1.

At step 302, a medical image of a nodule of a patient is received. The medical image may be directly received from a medical imaging system, such as, e.g., medical imaging system 104 of FIG. 1. Alternatively, the medical image may be received by loading a previously acquired medical image from a storage or memory of a computer system or receiving a medical image that has been transmitted from a remote computer system. The medical image may be of any suitable modality, but is preferably a three-dimensional (3D) CT image. In one embodiment, the medical image is an image of the lungs of the patient depicting one or more pulmonary nodules. However, it should be understood that the medical image may be of any region of interest of the patient depicting any subject of interest.

Figure 4:
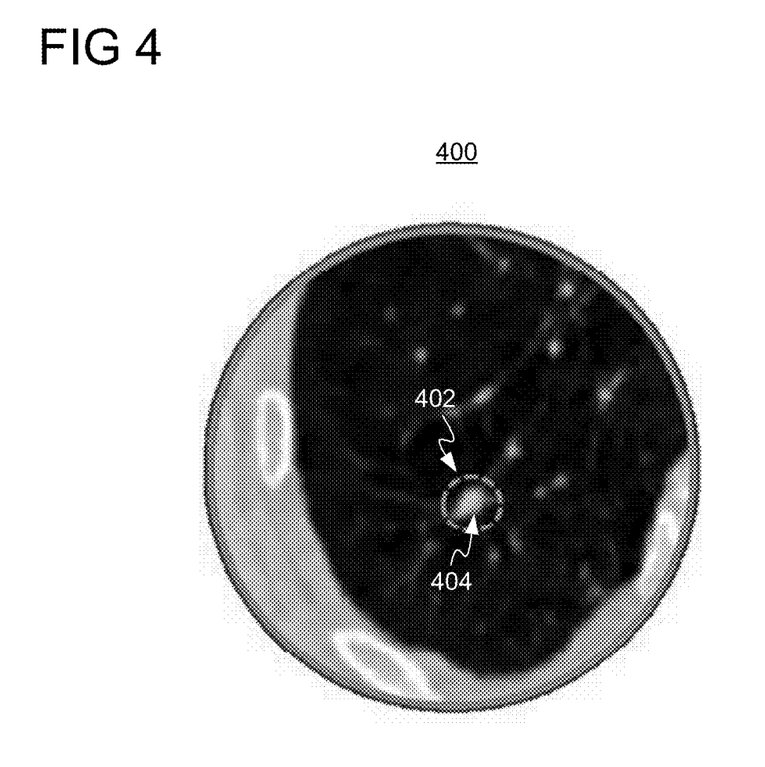
FIG. 4 shows an exemplary medical image of a lung of a patient having a nodule, in accordance with one or more embodiments.

At step 304, a patch surrounding the nodule is defined in the medical image of the patient. In one embodiment, the patch is a spatially local 3D patch surrounding the nodule in the medical image. The patch may be defined in the medical image using any suitable approach. In one embodiment, a deep reinforcement based algorithm is applied to identify the nodule in the medical image and define a patch surrounding the nodule. Accordingly, agents are trained to efficiently navigate the medical image to identify the nodule and define a patch surrounding the nodule. In another embodiment, 3D anisotropic hybrid networks may be utilized to leverage the full spatial resolution of the medical image to identify the nodule and define the patch surrounding the nodule. In another embodiment, a user (e.g., a clinician) may manually identify the nodule and define the patch surrounding the nodule. A patch surrounding a nodule is shown in FIG. 4.

At step 306, a malignancy of the nodule in the patch is predicted using a trained deep image-to-image network. In one embodiment, the deep image-to-image network is a deep reasoner network trained with a dense network and multi-task learning to predict a malignancy of the nodule. The deep image-to-image network is described in further detail below with respect to FIGS. 5-7.

The prediction of the malignancy of the nodule may be in any suitable form. In one embodiment, the malignancy of the nodule is predicted by classifying the nodule as being, e.g., malignant or not malignant (i.e., benign) or benign or not benign (i.e., malignant). In another embodiment, the malignancy of the nodule is predicted by determining a malignancy score indicating a malignancy of the nodule. For example, the malignancy score may be a score between zero and one, where a lower score (e.g., zero) indicates a greater confidence that the nodule is not malignant (i.e., benign) while a higher score indicates a greater confidence that the identified nodule is malignant.

At step 308, a medical decision for the nodule is made based on the predicted malignancy of the nodule. The medical decision may be any suitable medical decision. In one example, the medical decision may be whether or not to perform a biopsy for histopathological examination on the nodule of the patient. In one embodiment, the predicted malignancy may be used to confirm an analysis of a radiologist of the medical image in determining whether to perform a biopsy.

In one embodiment, where the predicted malignancy is the binary classification of malignant or not malignant, the medical decision is to perform the biopsy for histopathological examination on the nodule where the predicted malignancy is malignant, and to not perform the biopsy (and take no further action) on the nodule where the predicted malignancy is not malignant.

In another embodiment, where the predicted malignancy is a malignancy score, the medical decision is made based on the malignancy score with respect to one or more thresholds. For example, if the malignancy score is below a first threshold of, e.g., 0.2, the medical decision is to not perform the biopsy (and take no further action) on the nodule. If the malignancy score is between the first threshold and a second threshold of, e.g., 0.5, the medical decision is to receive or acquire a more detailed medical image (e.g., a positron emission tomography scan) of the nodule for further analysis. Accordingly, steps 302-308 may be repeated for the more detailed medical image. If the malignancy score is above the second threshold, the medical decision is to perform a biopsy for histopathological examination on the nodule.

FIG. 4 shows a medical image 400 of a lung of a patient, in accordance with one or more embodiments. Medical image 400 depicts pulmonary nodule 404. As shown in FIG. 4, patch 402 surrounding nodule 404 is identified. Patch 402 may be a spatially local 3D patch surrounding nodule 404. Patch 402 may be defined in medical image 400 using any suitable approach, such as, e.g., deep reinforcement based algorithms or 3D anisotropic hybrid networks. In one embodiment, patch 402 is the patch identified at step 304 of FIG. 3.

Figure 5:
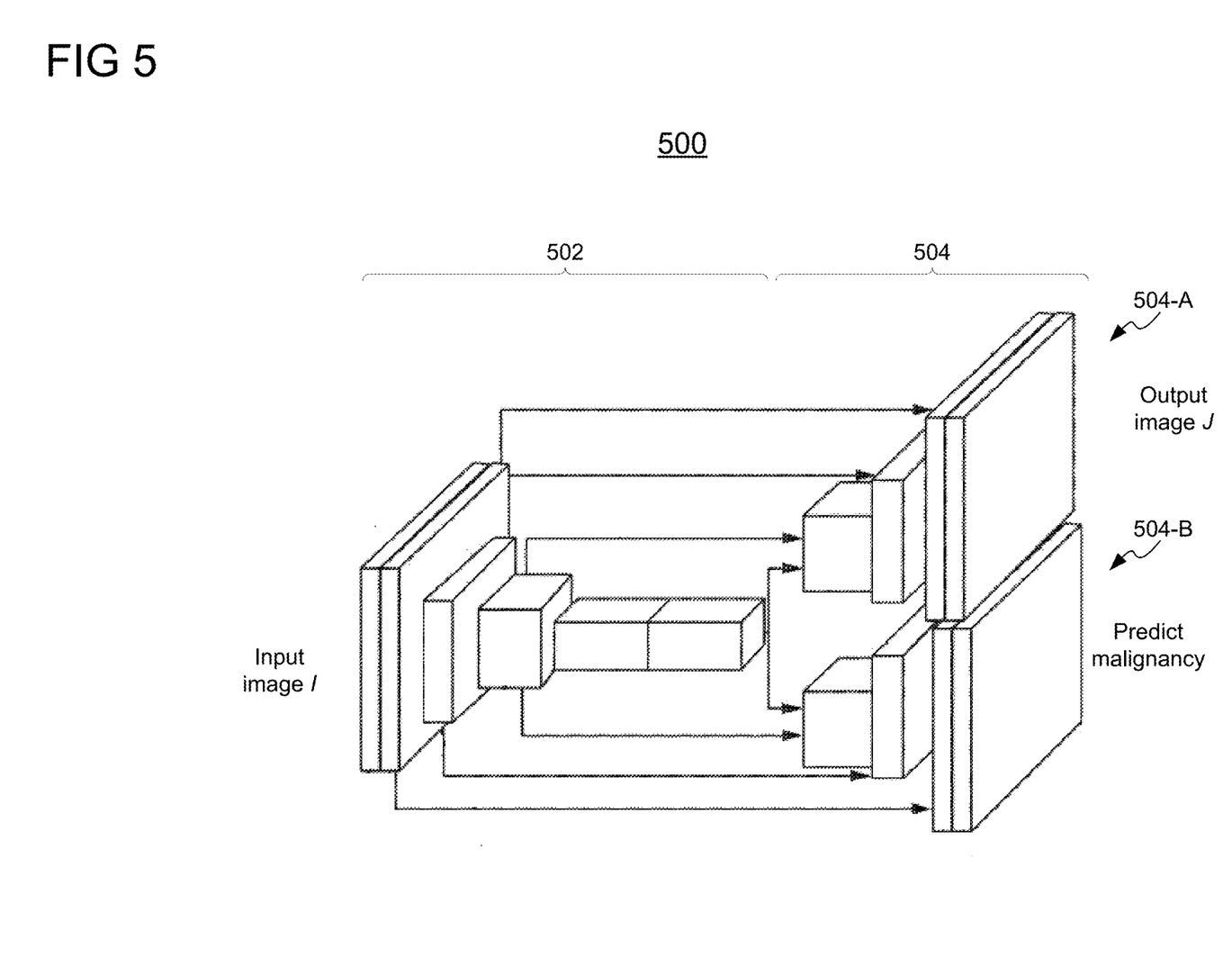
FIG. 5 shows network architecture of a deep image-to-image network for predicting a malignancy of a nodule of a patient, in accordance with one or more embodiments.

FIG. 5 illustrates a network architecture 500 of a deep image-to-image network, in accordance with one or more embodiments. In one embodiment, the deep image-to-image network is a deep reasoner network with a dense network. The deep image-to-image network is trained with multi-task learning to generate an output image J as a reconstruction of an input image I, and to predict a malignancy of a nodule in input image I. In one embodiment, the deep image-to-image network is trained and applied as described with respect to FIG. 7.

Network architecture 500 of the deep image-to-image network comprises a series of layers 502 of an encoding network (or encoder) F and a series of layers 504 of a decoding network (or decoder) G. Encoder F receives input image I. In one embodiment, input image I is the patch identified at step 304 of FIG. 3 or patch 402 of FIG. 4. Layers 502 of encoder F code or convert the input image I to a low level representation, whose size is substantially less than the size of the input image I. For example, encoder F may condense information of input image I to a small subset of values representing its lowest level information. Layers 504 of decoder G are branched into layers 504-A for automatically generating an output image J as a reconstruction of an input image I, and layers 504-B for automatically predicting a malignancy of a nodule in input image I. Layers 504-A of decoder G will decode the low level representation from encoder F into an output image J, which is a reconstruction of input image I. This can be expressed as J=G(F (I)). Layers 504-B of decoder G will decode the low level representation from encoder F to predict a malignancy of a nodule in input image I. All the intermediate information generated in the encoder F is shared with the decoder G so that no information is lost in the encoding process.

The trained network architecture 500 of the deep image-to-image network may be applied during an inference stage to predict a malignancy of a nodule at step 306 of FIG. 3. Accordingly, layers 504-B of decoder G will decode the code from layers 502 of encoder F to predict the malignancy of the nodule, while layers 504-A of decoder G will not be used. Parameters of the deep image-to-image network may be adjusted to, e.g., weigh the predictions towards finding that the nodules are malignant.

Figure 6:
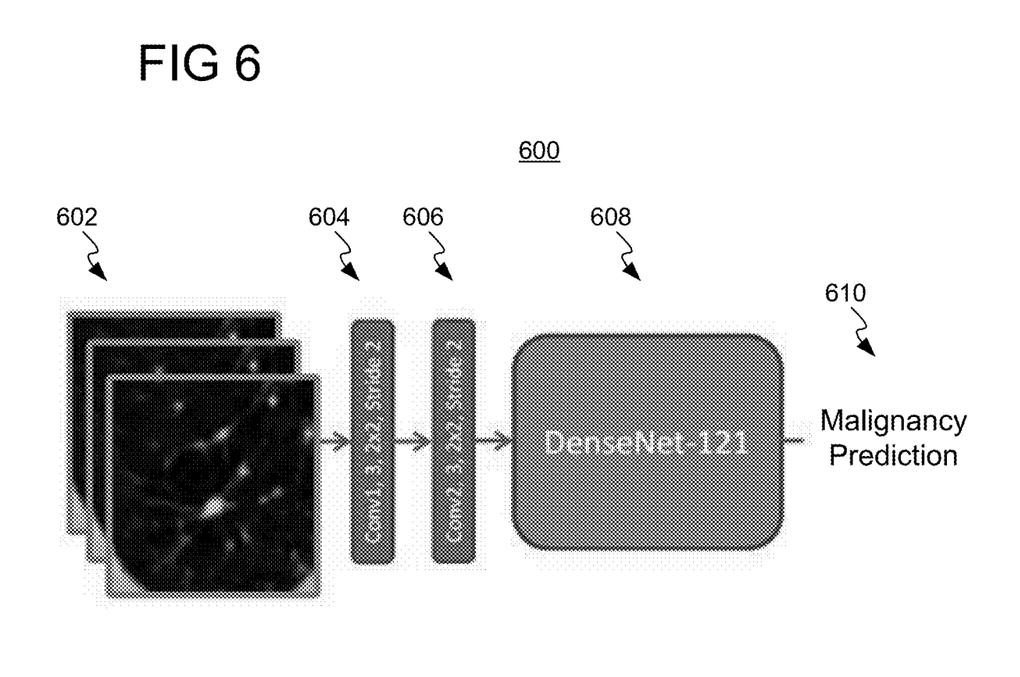
FIG. 6 shows a high-level network architecture for predicting a malignancy of a nodule of a patient, in accordance with one or more embodiments.

FIG. 6 shows a high-level network architecture 600 for predicting malignancy of a nodule, in accordance with one or more embodiments. One or more patches 602 surrounding nodules identified from medical images are input in a convolutional neural network (CNN) 604, whose output is input into CNN 606. In one embodiment, the one or more patches 602 may include the patch identified at step 304 of FIG. 3 or patch 402 of FIG. 4. CNNs 604 and 606 have a 2×2 filter and a stride of 2. The output of CNN 606 is input into a deep reasoner network with a dense network 608 trained to output a malignancy prediction 610 for the nodules. Malignancy prediction 610 may include, for example, classifying the nodules (e.g., malignant or not malignant), determining a malignancy score, etc. In one embodiment, the deep reasoner network with a dense network 608 is represented by network architecture 500 of FIG. 5.

Figure 7:
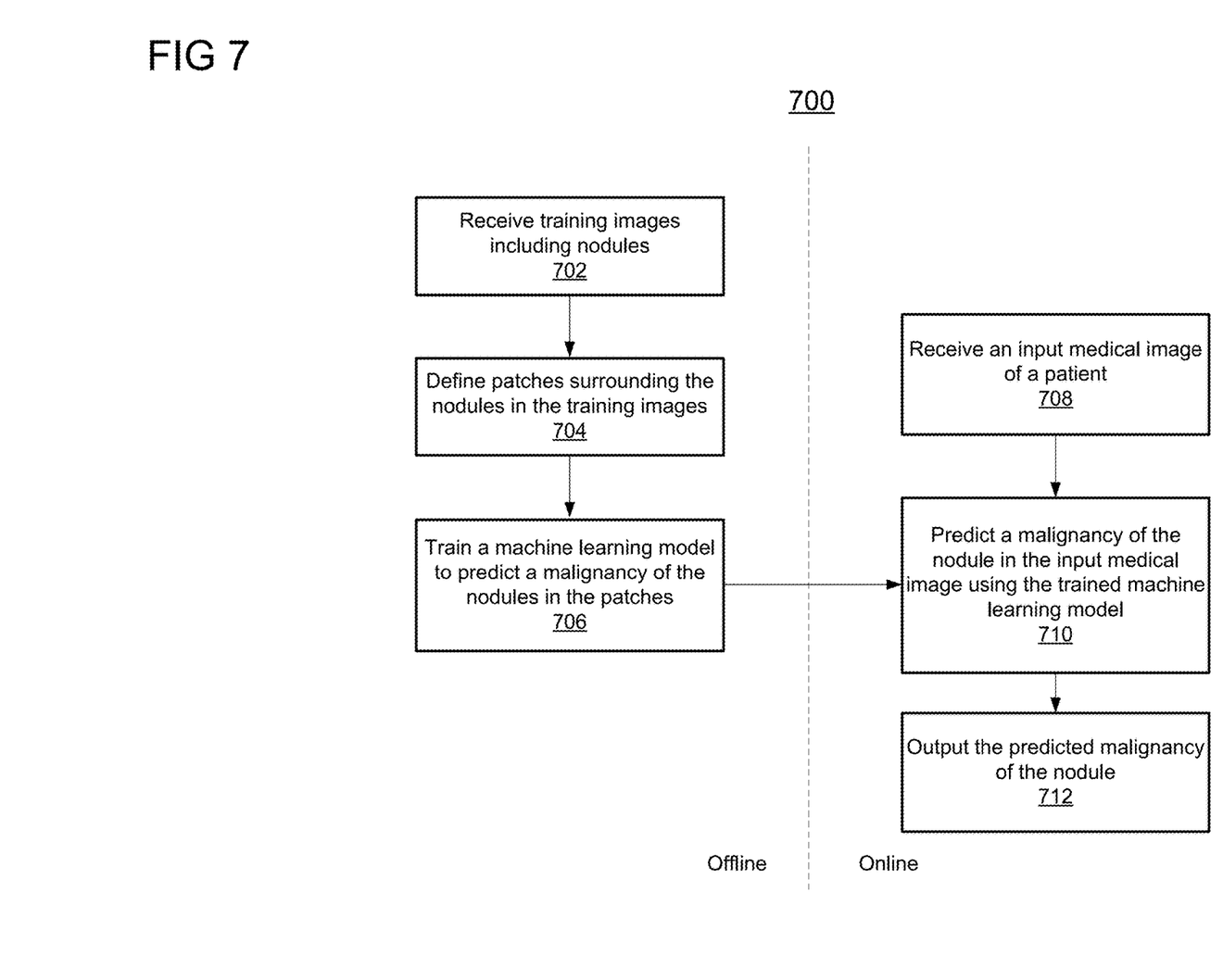
FIG. 7 shows a workflow for training and applying a machine learning model for predicting a malignancy of a nodule of a patient, in accordance with one or more embodiments.

FIG. 7 shows a workflow 700 for training and applying a machine learning model, in accordance with one or more embodiments. Steps 702-706 show an offline or training stage for training a machine learning model. Steps 708-712 show an online or inference stage for applying the trained machine learning model on newly received medical images. In one embodiment, step 306 of FIG. 3 is performed by performing the steps of the inference state (steps 708-712). The inference stage (steps 708-712) can be repeated for each newly received medical image(s). In one embodiment, the steps of workflow 700 may performed to train and apply the network architecture 500 of the deep image-to-image network in FIG. 5.

At step 702, during a training stage, training images including nodules are received. The training images are medical images acquired using a medical imaging modality corresponding to the modality of the input image to be analyzed during the inference stage (at step 706). For example, the modality may be computed tomography (CT), magnetic resonance (MR), DynaCT, ultrasound, x-ray, positron emission tomography (PET), etc. In one embodiment, the training images can be received by loading a number of previously stored medical training images from a database of medical images.

The training images may be annotated with ground truths indicating whether or not the nodules are malignant. In one embodiment, ground truths for a respective training image are determined by performing a biopsy on the nodule shown in the respective training image and performing histopathological examination of the biopsied nodule. In another embodiment, the ground truths may be determined based on a radiologist report of the biopsied nodule. While ground truths determined based on a radiologist report may not be as accurate as ground truths determined based on a histopathological examination, in some embodiments, ground truths determined based on a radiologist report may be used to supplement the ground truths determined based on a histopathological examination, e.g., where the ground truths determined based on a histopathological examination are insufficient to train the machine learning model. Generating training images annotated with ground truths is described in further detail below with respect to FIG. 8.

At step 704, patches surrounding the nodules in the training images are defined. The patches surrounding the nodules may be defined in the training images using any suitable approach, such as, e.g., the methods described above with respect to step 304 of FIG. 3. For example, the patches surrounding the nodules may be defined in the training images using a deep reinforcement based algorithm or 3D anisotropic hybrid networks.

In one embodiment, the training images received at step 702 are the patches surrounding the nodules. In this embodiment, step 704 may be skipped and the method may proceed to step 706 using the patches as the training images.

At step 706, a machine learning model is trained to predict a malignancy of the nodules in the patches. In one embodiment, the machine learning model is a deep image-to-image network, such as, e.g., a deep reasoner network with a dense network. In this embodiment, the deep image-to-image network is also trained to generate output images as reconstructions of the training images, as shown in network architecture 500 of FIG. 5. However, the deep image-to-image network to generate output images will not be used in the inference stage.

At step 708, during an inference stage, an input medical image of a patient is received. The input medical image comprises a patch surrounding a nodule. In one embodiment, the input medical image is the patch surrounding the nodule identified at step 304 of FIG. 3 or patch 402 of FIG. 4.

At step 710, a malignancy of the nodule in the input medical image is predicted using the trained machine learning model. The predicted malignancy may be a classification of the nodule (e.g., malignant or not malignant, benign or not benign, etc.), a malignancy score indicating a malignancy of the nodule, or any other suitable prediction.

At step 712, the predicted malignancy of the nodule is output. In one embodiment, the predicted malignancy of the nodule is output by returning the predicted malignancy to step 306 of FIG. 3. In some embodiments, the predicted malignancy of the nodule can be output by displaying the predicted malignancy on a display device of a computer system, storing the predicted malignancy on a memory or storage of a computer system, or by transmitting the predicted malignancy to a remote computer system.

It should be understood that once the machine learning model is trained during the training stage, the steps 708-712 of the inference stage can be repeated for each newly received input medical image(s). For example, blocks 708-712 can be repeated for each patch surrounding a nodule.

Figure 8:
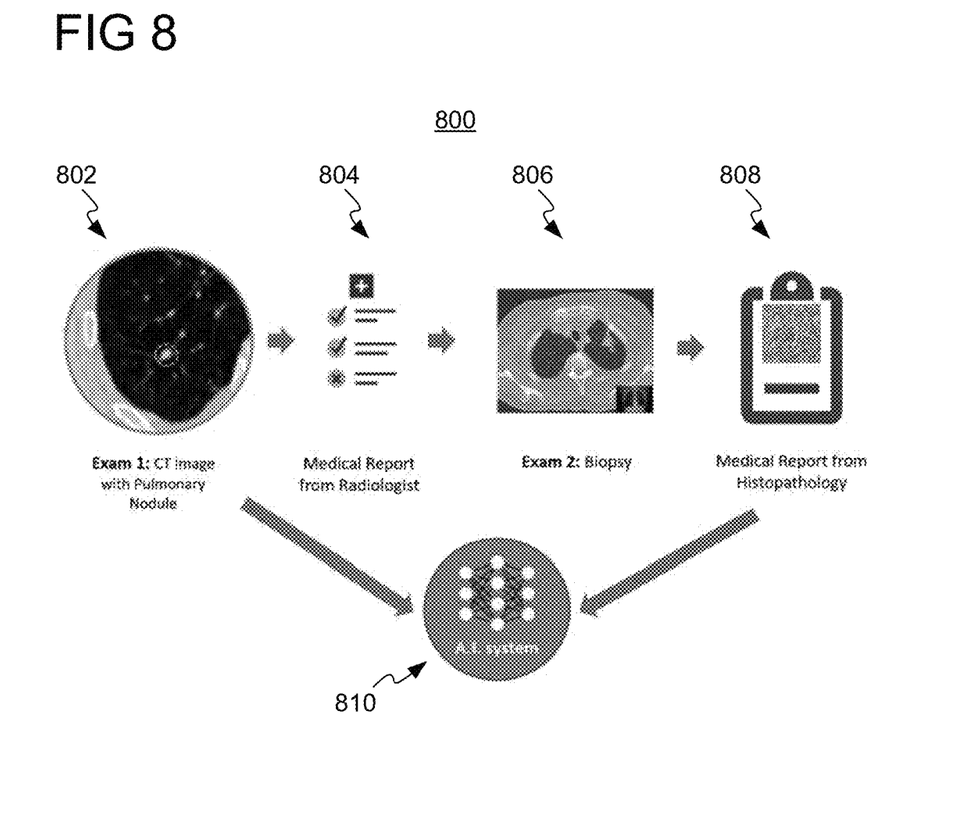
FIG. 8 shows a workflow for generating training data for training a machine learning model for predicting a malignancy of a nodule of a patient, in accordance with one or more embodiments.

FIG. 8 shows a workflow 800 for generating training data for training a machine learning model for predicting a malignancy of a nodule of a patient, in accordance with one or more embodiments. In one embodiment, the training data generated by performing workflow 800 may be the training images received at step 702 of the training stage of FIG. 7.

At step 802, a first examination (Exam 1) is performed to acquire CT medical images having pulmonary nodules for a population of patients. At step 804, a radiologist analyzes the CT medical images to identify the pulmonary nodules and generate a radiologist medical report. At step 806, a second examination (Exam 2) is performed by performing a biopsy on the pulmonary nodules. At step 808, a histopathological examination is performed on the biopsied pulmonary nodules to determine whether the pulmonary nodules are malignant. At step 810, the CT medical images acquired at step 802 are associated with the results of the histopathological examination determined at step 808 as ground truths for training an A.I system (e.g., a deep image-to-image network) to predict a malignancy of the pulmonary nodules.

In some embodiments, results of the radiologist analysis determined at step 804 may alternatively or additionally be used as the ground truths. While the results of the radiologist analysis determined at step 804 may not be as accurate as the results of the histopathological examination determined at step 808, in some embodiments, the results of the radiologist analysis can be used to supplement the results of the histopathological examination where, for example, there is an insufficient amount of results of the histopathological examination for training the A.I. system.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 2-3 and 7-8. Certain steps or functions of the methods and workflows described herein, including one or more of the steps or functions of FIGS. 2-3 and 7-8, may be performed by a server or by another processor in a network-based cloud-computing system. Certain steps or functions of the methods and workflows described herein, including one or more of the steps of FIGS. 2-3 and 7-8, may be performed by a client computer in a network-based cloud computing system. The steps or functions of the methods and workflows described herein, including one or more of the steps of FIGS. 2-3 and 7-8, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 2-3 and 7-8, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 9:
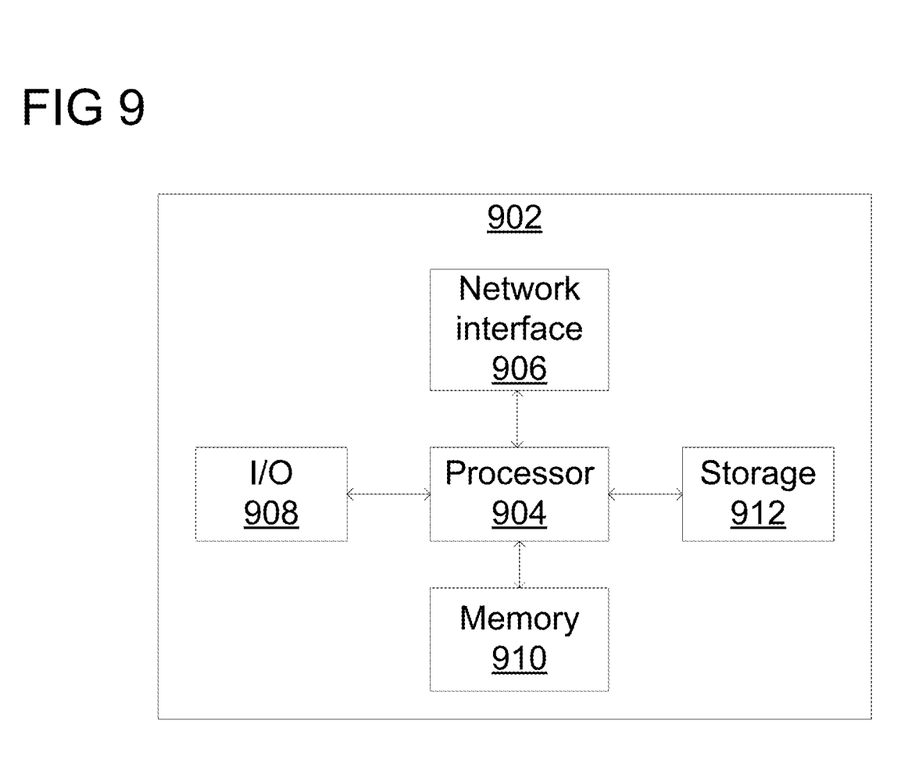
FIG. 9 shows a high-level block diagram of a computer.

A high-level block diagram of an example computer 902 that may be used to implement systems, apparatus, and methods described herein is depicted in FIG. 9. Computer 902 includes a processor 904 operatively coupled to a data storage device 912 and a memory 910. Processor 904 controls the overall operation of computer 902 by executing computer program instructions that define such operations. The computer program instructions may be stored in data storage device 912, or other computer readable medium, and loaded into memory 910 when execution of the computer program instructions is desired. Thus, the method and workflow steps or functions of FIGS. 2-3 and 7-8 can be defined by the computer program instructions stored in memory 910 and/or data storage device 912 and controlled by processor 904 executing the computer program instructions. For example, the computer program instructions can be implemented as computer executable code programmed by one skilled in the art to perform the method and workflow steps or functions of FIGS. 2-3 and 7-8. Accordingly, by executing the computer program instructions, the processor 904 executes the method and workflow steps or functions of FIGS. 2-3 and 7-8. Computer 904 may also include one or more network interfaces 906 for communicating with other devices via a network. Computer 902 may also include one or more input/output devices 908 that enable user interaction with computer 902 (e.g., display, keyboard, mouse, speakers, buttons, etc.).

Processor 904 may include both general and special purpose microprocessors, and may be the sole processor or one of multiple processors of computer 902. Processor 904 may include one or more central processing units (CPUs), for example. Processor 904, data storage device 912, and/or memory 910 may include, be supplemented by, or incorporated in, one or more application-specific integrated circuits (ASICs) and/or one or more field programmable gate arrays (FPGAs).

Data storage device 912 and memory 910 each include a tangible non-transitory computer readable storage medium. Data storage device 912, and memory 910, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 908 may include peripherals, such as a printer, scanner, display screen, etc. For example, input/output devices 908 may include a display device such as a cathode ray tube (CRT) or liquid crystal display (LCD) monitor for displaying information to the user, a keyboard, and a pointing device such as a mouse or a trackball by which the user can provide input to computer 902.

Any or all of the systems and apparatus discussed herein, including elements of workstation 102 of FIG. 1, may be implemented using one or more computers such as computer 902.

One skilled in the art will recognize that an implementation of an actual computer or computer system may have other structures and may contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for determining a malignancy of a nodule, comprising:
   receiving a medical image of a nodule of a patient;
   defining a patch surrounding the nodule in the medical image;
   predicting a malignancy of the nodule in the patch using a trained deep image-to-image network comprising an encoder and a decoder;
   comparing the predicted malignancy of the nodule in the patch with one or more thresholds;
   in response to the comparing of the predicted malignancy of the nodule in the patch with the one or more thresholds:
      receiving a second medical image of the nodule, the second medical image being of a different modality than the medical image and more detailed than the medical image;
      defining a second patch surrounding the nodule in the second medical image; and
      predicting a malignancy of the nodule in the second patch using the trained deep image-to-image network,
   wherein the trained deep image-to-image network is trained to, based on low level representations of training patches determined by the encoder, 1) reconstruct the training patches by a first branch of layers of the decoder and 2) predict a malignancy of nodules in the training patches by a second branch of layers of the decoder, and
   wherein the second branch of layers of the decoder is used to perform the predicting of the malignancy of the nodule in the patch without using the first branch of layers of the decoder.

2. The method of claim 1, further comprising:
   training the trained deep image-to-image network using the training images and results of a histopathological examination of the nodules in the training images.

3. The method of claim 2, wherein training the trained deep image-to-image network using the training images and results of a histopathological examination of the nodules in the training images further comprises:
   training the trained deep image-to-image network using additional training images and results of a radiologist examination of nodules in the additional training images.

4. The method of claim 1, wherein predicting a malignancy of the nodule in the patch using a trained deep image-to-image network comprises:
   determining a score indicating the malignancy of the nodule.

5. The method of claim 1, wherein predicting a malignancy of the nodule in the patch using a trained deep image-to-image network comprises:
   classifying the nodule as malignant or not malignant.

6. The method of claim 1, wherein predicting a malignancy of the nodule in the patch using a trained deep image-to-image network comprises:
   inputting the patch into the encoder for converting the patch to a low level representation; and predicting the malignancy of the nodule in the patch from the low level representation by the decoder.

7. The method of claim 1, wherein the trained deep image-to-image network comprises a trained deep reasoner network.

8. An apparatus for determining a malignancy of a nodule, comprising:
  means for receiving a medical image of a nodule of a patient;
  means for defining a patch surrounding the nodule in the medical image; and
  means for predicting a malignancy of the nodule in the patch using a trained deep image-to-image network comprising an encoder and a decoder;
  means for comparing the predicted malignancy of the nodule in the patch with one or more thresholds;
  in response to the comparing of the predicted malignancy of the nodule in the patch with the one or more thresholds:
    means for receiving a second medical image of the nodule, the second medical image being of a different modality than the medical image and more detailed than the medical image;
    means for defining a second patch surrounding the nodule in the second medical image; and
    means for predicting a malignancy of the nodule in the second patch using the trained deep image-to-image network,
  wherein the trained deep image-to-image network is trained to, based on low level representations of training patches determined by the encoder, 1) reconstruct the training patches by a first branch of layers of the decoder and 2) predict a malignancy of nodules in the training patches by a second branch of layers of the decoder, and
  wherein the second branch of layers of the decoder is used to perform the predicting of the malignancy of the nodule in the patch without using the first branch of layers of the decoder.

9. The apparatus of claim 8, further comprising:
  means for training the trained deep image-to-image network using the training images and results of a histopathological examination of the nodules in the training images.

10. The apparatus of claim 9, wherein the means for training the trained deep image-to-image network using the training images and results of a histopathological examination of the nodules in the training images further comprises:
  means for training the trained deep image-to-image network using additional training images and results of a radiologist examination of nodules in the additional training images.

11. The apparatus of claim 8, wherein the means for predicting a malignancy of the nodule in the patch using a trained deep image-to-image network comprises:
  means for determining a score indicating the malignancy of the nodule.

12. The apparatus of claim 8, wherein the means for predicting a malignancy of the nodule in the patch using a trained deep image-to-image network comprises:
  means for classifying the nodule as malignant or not malignant.

13. A non-transitory computer readable medium storing computer program instructions for determining a malignancy of a nodule, the computer program instructions when executed by a processor cause the processor to perform operations comprising:
  receiving a medical image of a nodule of a patient;
  defining a patch surrounding the nodule in the medical image;
  predicting a malignancy of the nodule in the patch using a trained deep image-to-image network comprising an encoder and a decoder;
  comparing the predicted malignancy of the nodule in the patch with one or more thresholds;
  in response to the comparing of the predicted malignancy of the nodule in the patch with the one or more thresholds:
    receiving a second medical image of the nodule, the second medical image being of a different modality than the medical image and more detailed than the medical image;
    defining a second patch surrounding the nodule in the second medical image; and
    predicting a malignancy of the nodule in the second patch using the trained deep image-to-image network,
  wherein the trained deep image-to-image network is trained to, based on low level representations of training patches determined by the encoder, 1) reconstruct the training patches by a first branch of layers of the decoder and 2) predict a malignancy of nodules in the training patches by a second branch of layers of the decoder, and
  wherein the second branch of layers of the decoder is used to perform the predicting of the malignancy of the nodule in the patch without using the first branch of layers of the decoder.

14. The non-transitory computer readable medium of claim 13, the operations further comprising:
  training the trained deep image-to-image network using the training images and results of a histopathological examination of the nodules in the training images.

15. The non-transitory computer readable medium of claim 13, wherein predicting a malignancy of the nodule in the patch using a trained deep image-to-image network comprises:
  inputting the patch into the encoder for converting the patch to a low level representation; and
  predicting the malignancy of the nodule in the patch from the low level representation by the decoder.

16. The non-transitory computer readable medium of claim 13, wherein the trained deep image-to-image network comprises a trained deep reasoner network.

* * * * *